(12) United States Patent
Vijayanagar

(10) Patent No.: US 8,556,809 B2
(45) Date of Patent: Oct. 15, 2013

(54) SURGICAL TISSUE RETRACTOR

(76) Inventor: Raghavendra Rao Vijayanagar, Tampa, FL (US)

( * ) Notice: Subject to any disclaimer, the term of this patent is extended or adjusted under 35 U.S.C. 154(b) by 25 days.

(21) Appl. No.: 13/134,618

(22) Filed: Jun. 10, 2011

(65) Prior Publication Data
US 2012/0316400 A1 Dec. 13, 2012

(51) Int. Cl.
*A61B 1/32* (2006.01)
(52) U.S. Cl.
USPC ......................................................... 600/235
(58) Field of Classification Search
USPC ......... 600/201, 222, 224, 232, 233, 235, 236; 403/165; 24/460, 462, 490, 491, 499
See application file for complete search history.

(56) References Cited

U.S. PATENT DOCUMENTS 2,707,052 A * 4/1955 Brown ........................... 211/65
6,837,851 B1 * 1/2005 Valentini et al. .............. 600/210

* cited by examiner

*Primary Examiner* — Kevin T Truong
*Assistant Examiner* — Christian Sevilla
(74) *Attorney, Agent, or Firm* — Arthur W. Fisher, III

(57) ABSTRACT

A surgical tissue retractor for use in aortic or pulmonary valve surgery coupled to a sternal retractor or similar base comprising a retractor assembly including a retractor support to operatively support a plurality of radially adjustable retractor blades to engage and retain a heart valve open during a surgical procedure, a retractor coupling assembly including a retractor connecting member coupled to the retractor support frame by a support frame mount and adjustably coupled to the sternum by a sternal retractor mount to operatively position and maintain the radially adjustable retractor blades in place during the surgical procedure.

18 Claims, 5 Drawing Sheets

SURGICAL TISSUE RETRACTOR

BACKGROUND OF THE INVENTION

1. Field of the Invention

A surgical tissue retractor for aortic or pulmonary surgery to engage and retain a heart valve open during the surgery.

2. Description of the Prior Art

The aortic and the pulmonary valve are tri-leaflet in nature. During aortic or pulmonary valve surgery the diseased valve needs to be held open to expose the valve for correction or replacement of the valve. This requires a valve retractor.

Chest retractors exist in many sizes and shapes for cardiac surgery. Many such chest retractors have an elongate rack bar and two retracting arms, namely a fixed retracting arm and a movable retracting arm. Both arms typically extend in a direction normal to the rack bar. The movable arm can be displaced along the rack bar, and relative to the fixed arm, by using a crank to activate a pinion mechanism which engages teeth on the rack bar. Two blades are provided, usually disposed below the retractor arm and extending into the surgical incision, to interface with the patient's skin and thoracic bone structure. These two blades apply the retraction that creates the surgical window by the relative movement and an ensuing spacing apart of the two retractor arms.

U.S. Pat. No. 6,837,851 and US 2005/0096508 show a surgical tool for retracting body tissue during surgery comprising two pivoting arms each provided with a finger, a translating actuation member also provided with a finger, and a single actuator mechanically coupled to either one of the pivoting arms or the translating actuation member. The two pivoting arms and the actuation member are operatively connected together for simultaneous movement between a closed configuration having the three fingers close together, and an open configuration having the three fingers spaced apart. The surgical tool is adaptable to suit the specific patient anatomy and desired degree of tissue retraction.

US 2010/0286485 relates to an adjustable multi-bladed tissue retractor capable of producing an incrementally variable or fine-tunable retracted opening in a surgical incision or a body cavity comprising an actuator coupled to a retractor housing and a movable linkage arrangement capable of moving the plurality of tissue-engaging blades attached thereto between a closed-blade configuration and an open-blade configuration. Through the application of a predetermined input to the actuator, a controlled, or selectable spaced apart spatial relationship of the plurality of tissue are positioned for retracting blades for the specific anatomy of the patient.

US 2011/0046448 describes a tissue retracting apparatus for use in cardiac surgery having a first tissue retracting member configured and sized to retract a cardiac tissue of the patient's heart and a second tissue retracting member configured and sized to retract, depress or displace a valve cusp tissue of the target heart valve. In use, the second tissue retracting member is coupled to the first retracting member, so that the first and second retracting members cooperate together to collectively allow the simultaneous retraction of a cardiac tissue of the patient's heart and a valve cusp of the target valve while a surgical intervention can be carried out on either the target heart valve or a subvalvular structure of the target heart valve.

Additional examples of the prior art are found in: U.S. Pat. No. 6,074,343; U.S. D 430,294; U.S. D 422,705 and U.S. D 448,081.

SUMMARY OF THE INVENTION

The present invention relates to a surgical tissue retractor for use in aortic or pulmonary valve surgery comprising a retractor assembly and a retractor coupling assembly.

The retractor assembly comprises a retractor support frame to operatively support a plurality of radially adjustable retractor blades The retractor coupling assembly comprises a retractor connector adjustably coupled to the retractor support frame by a support frame mount.

The retractor support frame comprises a circular ring including a plurality of holes or channels to receive a portion of a corresponding radially adjustable retractor blade therethrough. Each radially adjustable retractor blade comprises a valve engaging blade element coupled to the circular ring of the retractor support frame. A retractor blade retainer may be provided to lock or retain each valve engaging blade element of each radially adjustable retractor blade in operative position during a surgical procedure once each radially adjustable retractor blade is adjusted relative to the circular ring and the heart valve.

The valve engaging blade element comprises a pendant member including a lower valve retainer to engage and retain the heart valve open during a surgical procedure. The lower valve retainer comprises an upwardly flared skirt including an arcuate or convex valve engaging surface.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
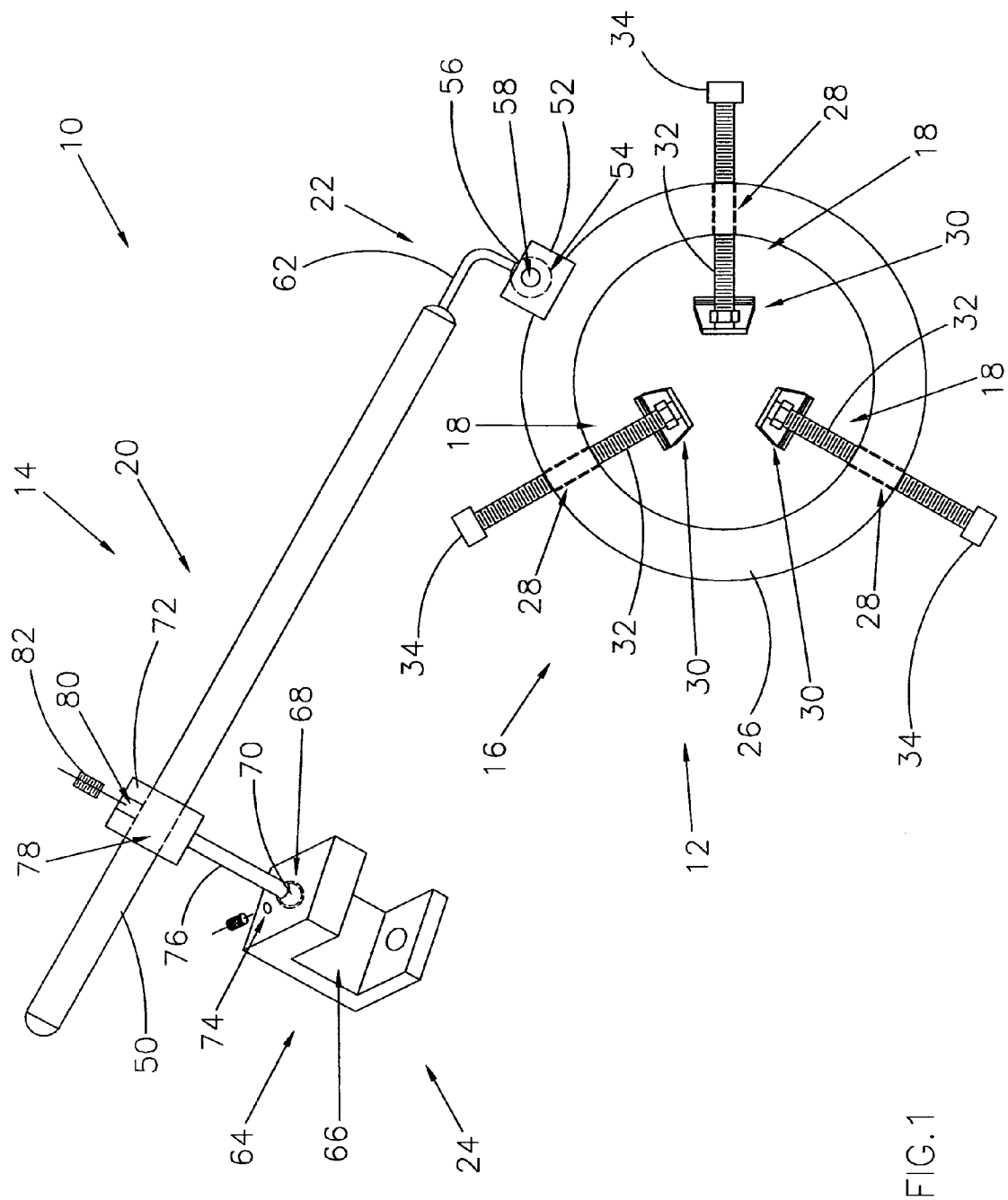
FIG. 1 is a top view of the surgical tissue retractor of the present invention.
Figure 2:
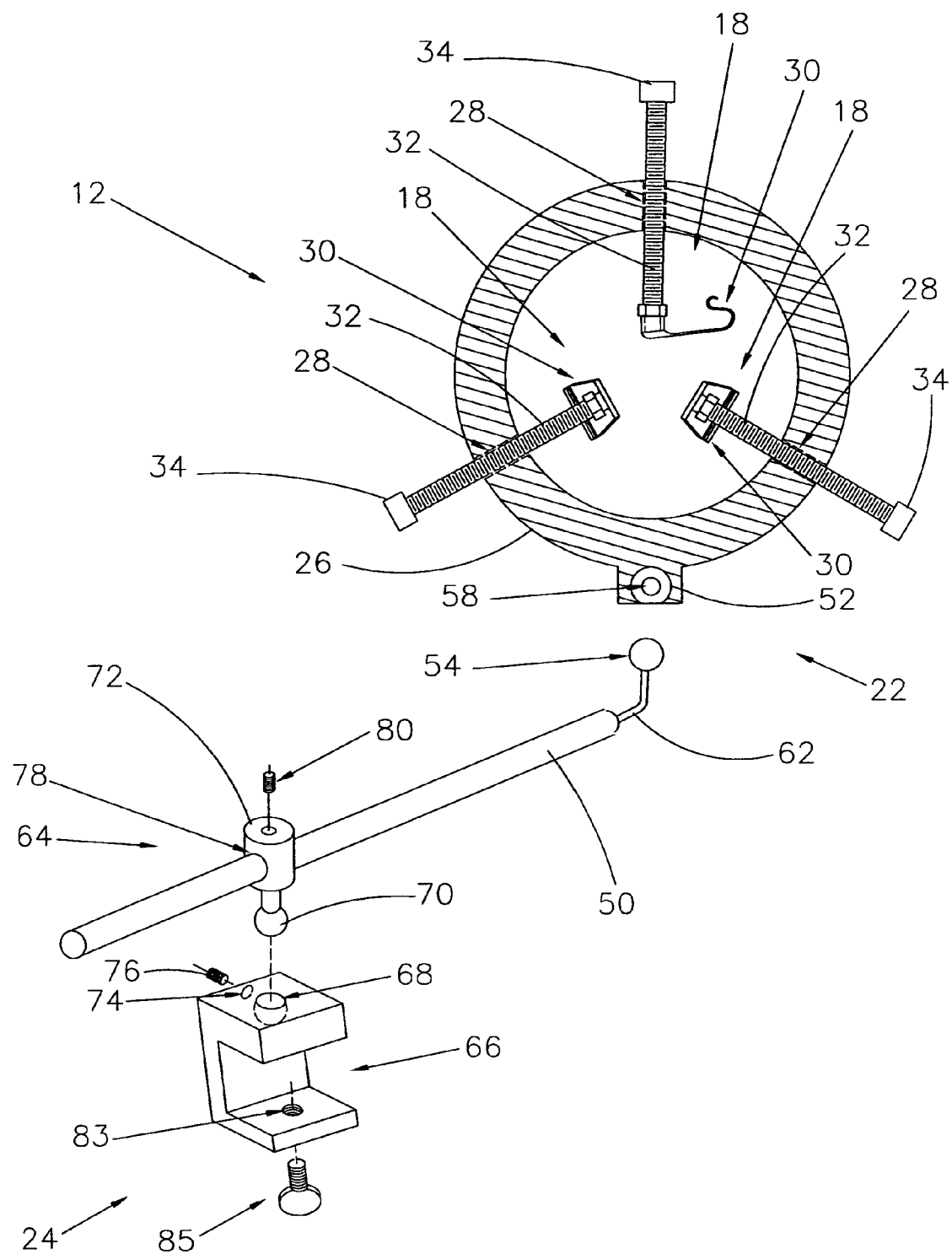
FIG. 2 is a perspective view of the surgical tissue retractor of the present invention.
Figure 3:
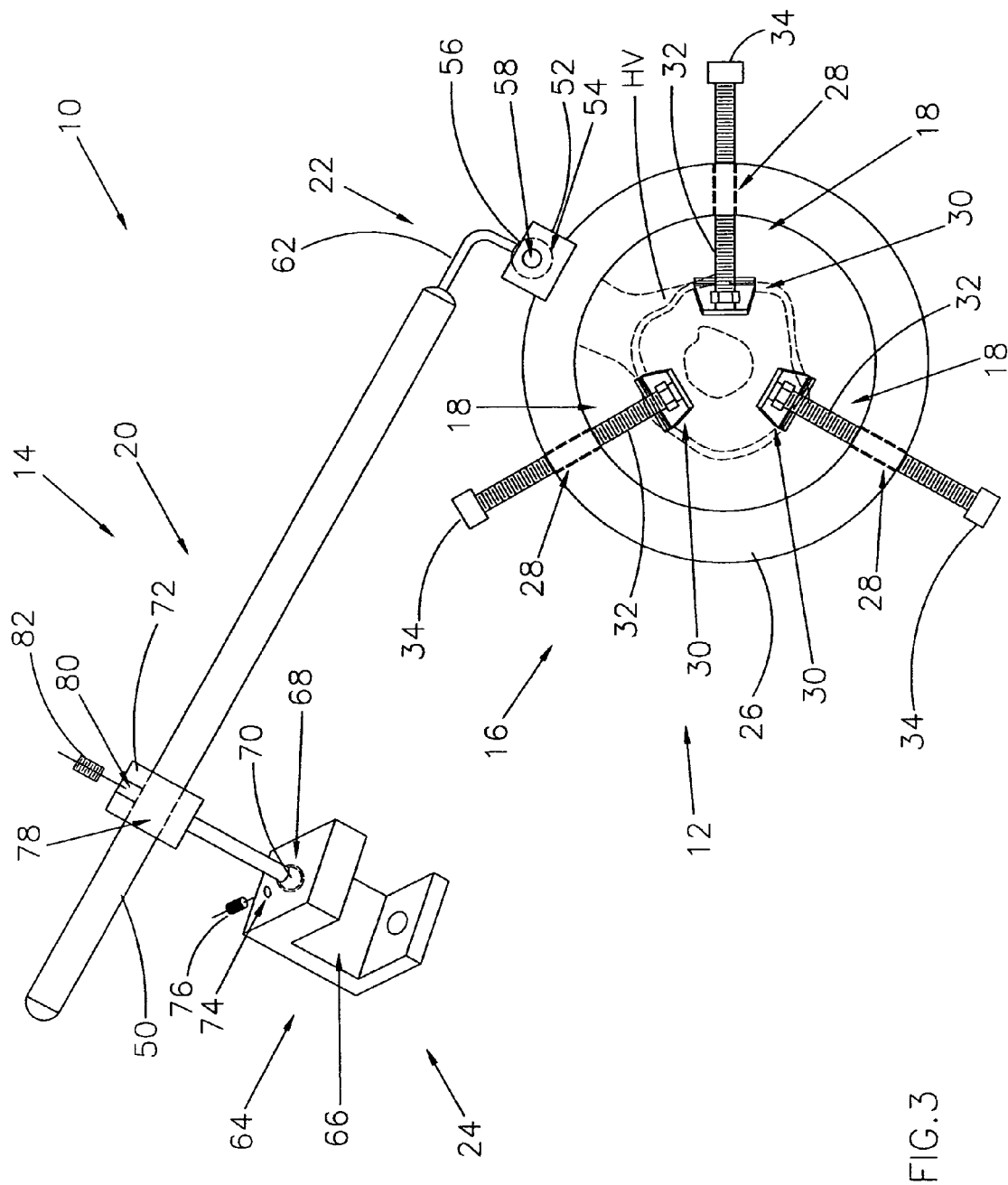
FIG. 3 is a top view of the surgical tissue retractor of the present invention holding a heart valve open.

As shown in FIGS. 1 through 3, the present invention relates to a surgical tissue retractor generally indicated as 10 for use in aortic or pulmonary valve surgery. The surgical tissue retractor 10 may be coupled to or mounted on a sternal retractor (not shown) or similar base during the surgical procedure. The surgical tissue retractor 10 comprises a retractor assembly generally indicated as 12 and a retractor coupling assembly generally indicated as 14.

The retractor assembly 12 comprises a retractor support frame generally indicated as 16 to operatively support a plurality of radially adjustable retractor blades each generally indicated as 18.

The retractor coupling assembly 14 comprises a retractor connector generally indicated as 20 adjustably coupled to the retractor support frame 16 by a support frame mount generally indicated as 22 and to the sternal retractor (not shown) by a sternal retractor mount generally indicated as 24.

The retractor support frame 16 comprises a circular ring 26 including a plurality of holes or channels each indicated as 28 to receive a portion of a corresponding radially adjustable retractor blade 18 therethrough as described hereinafter. As depicted, the radially adjustable retractor blades 18 are symmetrically or equally spaced around the circular ring 26. Each radially adjustable retractor blade 18 comprises a valve engaging blade element generally indicated as 30 coupled to the circular ring 26 of the retractor support frame 16 by a corresponding elongated rod 32 extending through a corresponding hole or channel 28. The elongated rod 32 shown in FIGS. 1 through 3 are externally threaded, while, the holes or channels 28 are internally threaded such that each radially adjustable retractor blade 18 is movable radially relative to the circular ring 26 of the retractor support frame 16 whereby each valve engaging blade element 30 engages the heart valve HV to retain the heart valve in an open position during a surgical procedure as shown in FIG. 3 by simply rotating each elongated rod 32 within the corresponding internally threaded hole or channel 28. Each radially adjustable retractor blade 18 may include an enlarged member 34 formed in the outer end portion of the corresponding elongated rod 32 to facilitate rotation of the corresponding radially adjustable retractor blade 18 to adjust the radially adjustable retractor blades 18 relative to the circular ring 26 of the retractor assembly 12.

Figure 4:
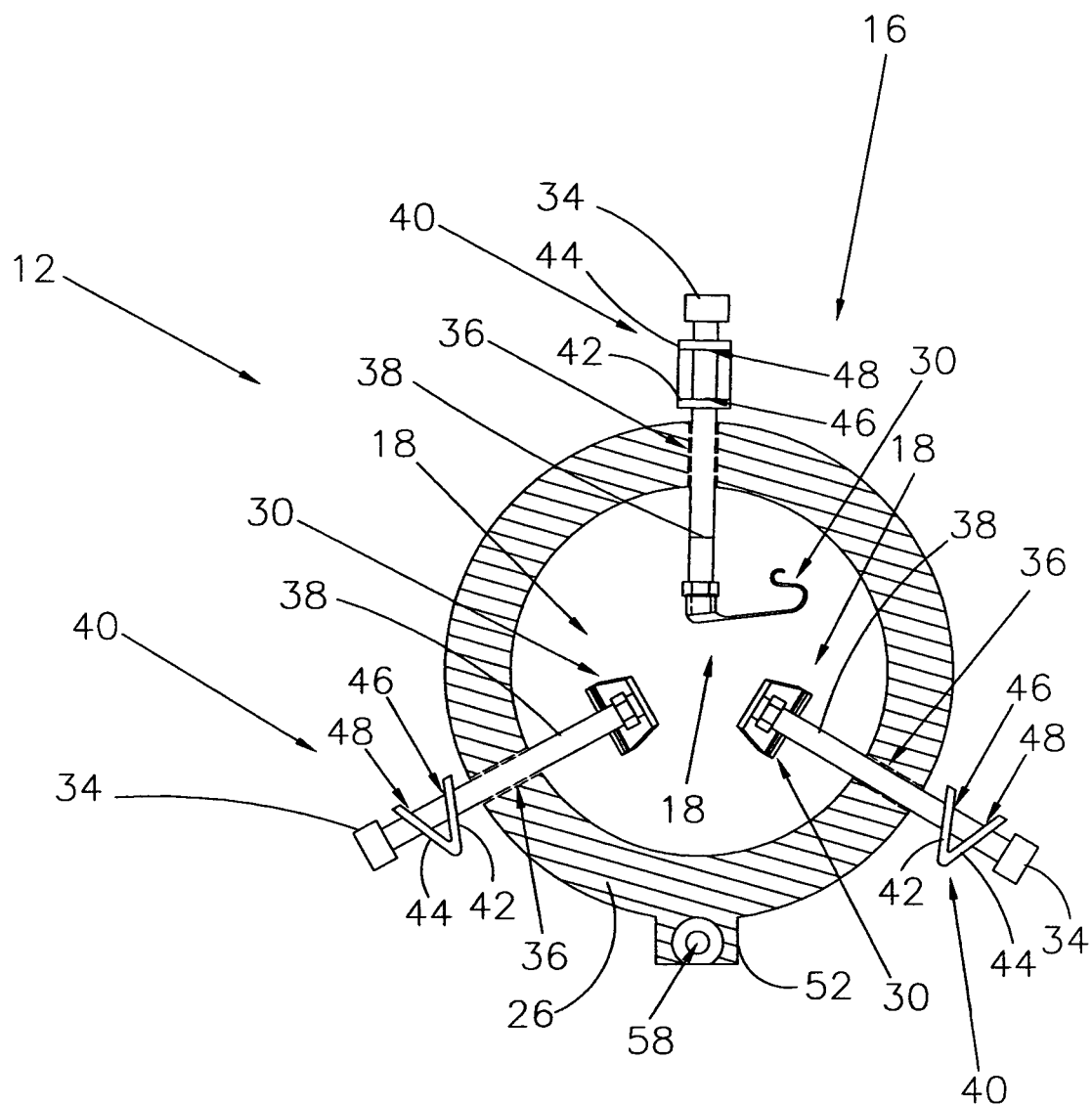
FIG. 4 is a detailed top view of an alternate embodiment of the retractor assembly of the present invention.

An alternate embodiment of the retractor assembly 12 is shown in FIG. 4. Similar structural elements are similarly designated as in FIGS. 1 through 3. Specifically, the retractor assembly 12 comprises a retractor support frame generally indicated as 16 to operatively support a plurality of radially adjustable retractor blades each generally indicated as 18.

The retractor coupling assembly 14 comprises a retractor connector generally indicated as 20 adjustably coupled to the retractor support frame 16 by a support frame mount generally indicated as 22 and to the sternal retractor (not shown) by a sternal retractor mount generally indicated as 24.

The retractor support frame 16 comprises a circular ring 26 including a plurality of holes or channels each indicated as 28 to receive a portion of a corresponding radially adjustable retractor blade 18 therethrough as described hereinafter. As depicted, the radially adjustable retractor blades 18 are symmetrically or equally spaced around the circular ring 26. Each radially adjustable retractor blade 18 comprises a valve engaging blade element generally indicated as 30 coupled to the circular ring 26 of the retractor support frame 16 by a corresponding elongated rod 32 extending through a corresponding hole or channel 28.

In contrast to the retractor assembly 12 of FIGS. 1 through 3, the retractor assembly of FIG. 4 includes smooth holes or channels 36 to receive correspondingly smooth elongated rods 38 therethrough. A retractor blade retainer generally indicated as 40 is provided to lock or retain each corresponding elongated rod 32 and valve engaging blade element 30 of each radially adjustable retractor blade 18 in operative position during a surgical procedure once each radially adjustable retractor blade 18 is adjusted relative to the circular ring 26 and the heart valve HV. Each retractor blade retainer 40 comprises a first retainer or locking element 42 disposed to engage the outer periphery of the circular ring and a second retainer or locking element 44 movable between a first or locked position and a second or unlocked position relative to the first retainer or locking element 42 to lock or secure the corresponding radially adjustable retainer blade 18 in place when in the first or locked position and to unlock the corresponding radially adjustable retainer blade 18 to permit radial adjustment of the corresponding radially adjustable retainer blades 18 relative to the circular ring 26 of the retractor support frame 16 when in the second or unlocked position. The first retainer or locking element 42 including a first aperture 46 and the second retainer or locking element 44 including a second aperture 48 to receive the corresponding elongated rod 38 of the corresponding radially adjustable retainer blade 18 therethrough cooperatively form a substantially v-shaped spring when the first retainer or locking element 42 and the second retainer or locking element 44 are each in the first or locked position such that when the second retainer or locking element 44 is moved from the first or locked position to the second or unlocked position by squeezing the first retainer or locking element 42 and the second retainer or locking element 44 together the first retainer or locking element 42 and the second retainer or locking element 44 are substantially parallel relative to each other axially aligning corresponding first apertures 46 and second apertures 48 relative to each other whereby the corresponding elongated rod 32 of the corresponding radially adjustable retractor blade 18 can be adjusted radially relative to the circular ring 26 of the retractor support frame 16 whereby each valve engaging element 30 of each retractor blade 18 is positioned to operatively engage a heart valve HV during a surgical procedure.

Each radially adjustable retractor blade 18 may include an enlarged member 34 formed in the outer end portion of the corresponding elongated rod 32 to facilitate rotation of the corresponding radially adjustable retractor blade 18 to adjust the radially adjustable retractor blades 18 relative to the circular ring 26 of the retractor assembly 12.

As shown in FIGS. 1 through 3, the retractor connector 20 comprises an elongated substantially cylindrical arm or member 50 coupled at opposite end portions to the support frame mount 22 and the sternal retractor mount 24.

The support frame mount 22 comprises a housing 52 affixed to the circular ring 26 of the retractor support frame 16 that includes a concave recess or seat 54 to receive and seat at least a portion of a convex member or sphere 56 therein and an internally threaded hole or channel 58 extending from the surface of the convex member or sphere 56 to the concave recess or seat 54 to receive an externally threaded fastener or thumbscrew 60 to engage the convex member or sphere 56 when positioned in the concave recess or seat 54 (FIG. 4) to selectively position and retain the retractor support frame 16 in position relative to the elongated substantially cylindrical arm or member 50. The elongated substantially cylindrical arm or member 50 is connected to the convex member or sphere 56 by a substantially L-shaped interconnecting member 62.

The sternal retractor mount 24 comprises a substantially u-shaped bracket generally indicated as 64 including a slot or channel 66 to mount the surgical tissue retractor 10 to a sternal retractor (not shown) and a concave recess or seat 68 to receive and seat at least a portion of a convex member or sphere 70 therein affixed to an interconnecting member 72 and an internally threaded hole or channel 74 to receive an externally threaded fastener 76 to secure at least a portion of the convex member or sphere 70 in the concave recess or seat 68. The interconnecting member 72 includes a channel or hole 78 formed therethrough to receive an end portion of the elongated substantially cylindrical arm or member 50 such that the elongated substantially cylindrical arm or member 50 is adjusted relative thereto and an internally threaded channel or hole 80 to receive an externally threaded fastener 82 to secure the interconnecting member 72 in place on the elongated substantially cylindrical arm or member 50.

Figure 5:
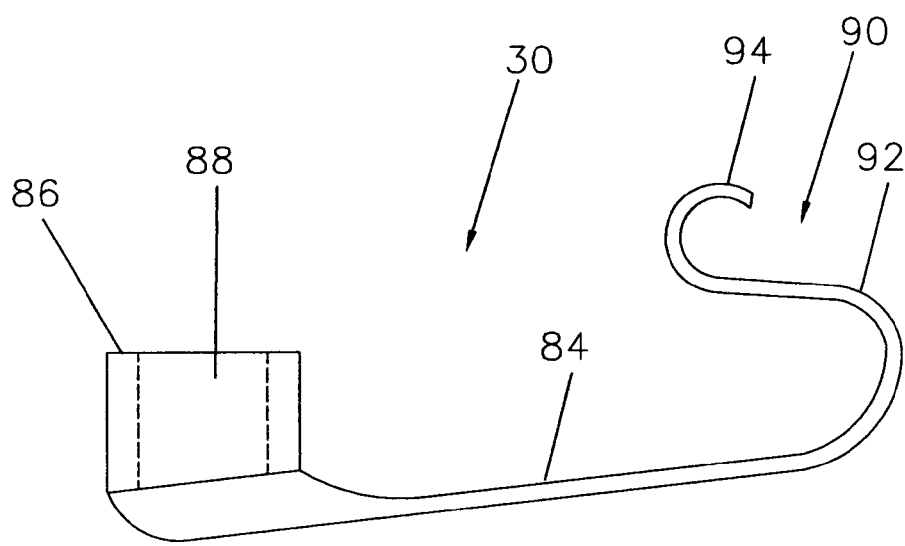
FIG. 5 is a side view of the valve engaging blade element.
Figure 5A:
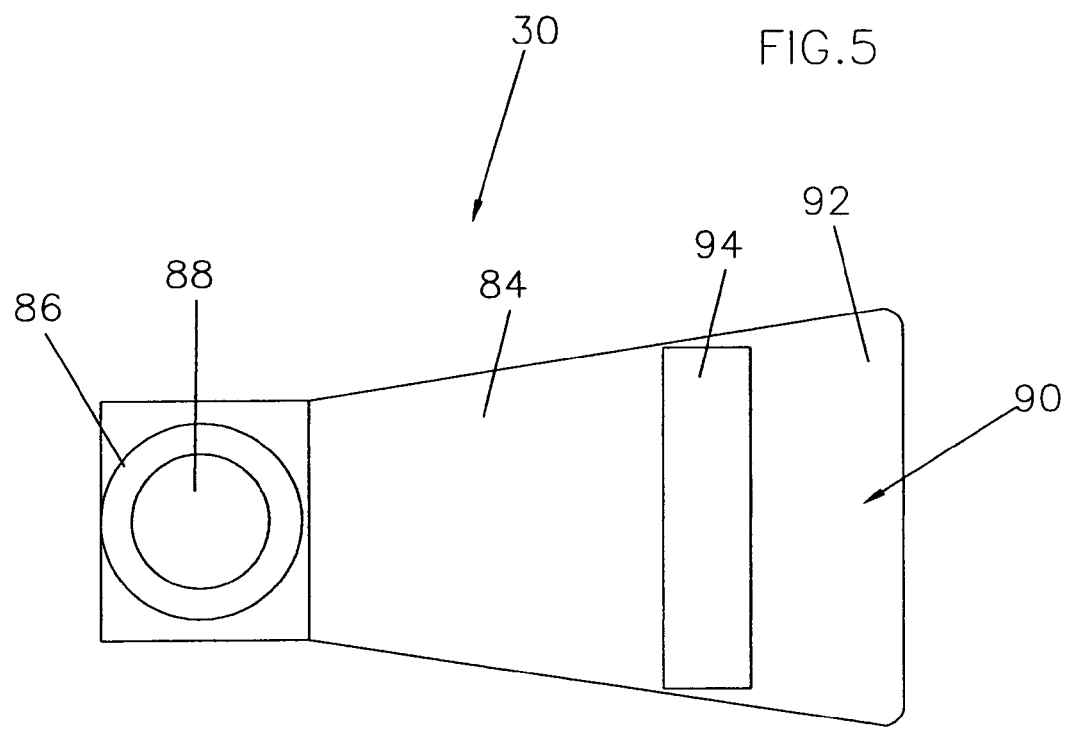
FIG. 5A is a front view of the valve engaging blade element.

FIGS. 5 and 5A show the valve engaging blade element 30 of the present invention. Specifically, the valve engaging blade element 30 comprises a pendant member 84 affixed to a corresponding elongated rod 32 by an upper mounting member 86 including a recess 88 to receive the outer portion of the corresponding elongated rod 32 and a lower valve retainer generally indicated as 90 to engage and retain the heart valve HV open during a surgical procedure. The lower valve retainer 90 comprises an upwardly flared skirt 92 including an arcuate or convex valve engaging surface 94 of at least 200 degrees disposed outwardly in spaced relationship relative to the pendant member 84 and beneath the upper mounting member 86.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. A surgical tissue retractor for use in aortic or pulmonary valve surgery comprising a retractor assembly including a retractor support frame having an outer periphery, a plurality of radially adjustable retractor blades configured to engage and retain a heart valve open during a surgical procedure mounted on said retractor support frame; and a retractor coupling assembly including a retractor connector adjustably coupled to said retractor support frame by a support frame mount to operatively position and maintain said radially adjustable retractor blades in place during the surgical procedure, wherein said retractor support frame comprises a circular ring including a plurality of holes or channels to receive a portion of a corresponding radially adjustable retractor blade therethrough, wherein each said radially adjustable retractor blade comprises a valve engaging blade element coupled to said retractor support frame by a corresponding rod extending through a corresponding hole or channel formed through said retractor support frame, wherein each said rod comprises an elongated rod such that each said radially adjustable retractor blade is movable axially relative to said circular ring of said retractor support frame whereby each said valve engaging blade element is capable of engaging the pulmonary or heart valve to retain the pulmonary or heart valve in an open position during a surgical procedure, and each rod further including a substantially v-shaped retractor blade retainer for each said radially adjustable retractor blade to retain each corresponding elongated rod and valve engaging blade element of each radially adjustable retractor blade in operative position during a surgical procedure once each radially adjustable retractor blade is adjusted relative to said retractor support frame, wherein each said retractor blade retainer comprises a first retainer or locking element disposed to engage said outer periphery of said retractor support frame and a second retainer or locking element movable between a first or locked position and a second or unlocked position relative to said first retainer or locking element to lock or secure the corresponding radially adjustable retainer blade in place when in said first or locked position and to unlock the corresponding radially adjustable retainer blade to permit radial adjustment of the corresponding radially adjustable retainer blades when in said second or unlocked position.

2. The surgical tissue retractor of claim 1 wherein said radially adjustable retractor blades are symmetrically spaced around said circular ring.

3. The surgical tissue retractor of claim 1 wherein each said first retainer or locking element includes a first aperture and each second retainer or locking element including a second aperture to receive the corresponding elongated rod of the corresponding radially adjustable retainer blade therethrough cooperatively form a substantially v-shaped spring when said first retainer or locking element and said second retainer or locking element are each in said first or locked position such that when said second retainer or locking element is moved from said first or locked position to said second or unlocked position said corresponding first aperture and second apertures are axially aligned relative to each other such that said corresponding elongated rod of the corresponding radially adjustable retractor blade is adjusted radially relative to said retractor support frame whereby each said valve engaging element of each retractor blade is positioned to operatively engage a heart valve during a surgical procedure.

4. The surgical tissue retractor of claim 1 wherein said retractor connector comprises an elongated arm or member coupled at opposite end portions to the support frame mount and a sternal retractor mount.

5. The surgical tissue retractor of claim 4 wherein said support frame mount comprises a housing affixed to said retractor support frame including a concave recess or seat that receives and seats at least a portion of a convex member therein and an internally threaded hole or channel extending from a surface of said convex member to said concave recess or seat to receive an externally threaded fastener to engage said convex member when positioned in said concave recess or seat to selectively position and retain said retractor support frame in position relative to the elongated arm or member.

6. The surgical tissue retractor of claim 5 wherein said elongated arm or member is connected to said convex member by a substantially L-shaped interconnecting member.

7. The surgical tissue retractor of claim 5 wherein said sternal retractor mount comprises a bracket including a slot to mount said surgical tissue retractor to a sternal retractor and a concave recess or seat that receives and seats at least a portion of a convex member therein affixed to an interconnecting member and an internally threaded hole or channel to receive an externally threaded fastener to secure at least a portion of the convex member in said concave recess or seat.

8. The surgical tissue retractor of claim 7 wherein said interconnecting member includes a channel or hole formed therethrough to receive an end portion of said elongated arm or member such that said elongated arm or member is adjusted relative thereto and an internal channel or hole to receive an externally threaded fastener to secure said interconnecting member in place relative to said elongated arm or member.

9. A surgical tissue retractor for use in aortic or pulmonary valve surgery comprising a retractor assembly including a retractor support frame having an outer frame, a plurality of radially adjustable retractor blades configured to engage and retain a heart valve open during a surgical procedure mounted on said retractor support frame, each retractor blade having an elongated rod positioned in a hole or channel formed in the retractor support frame and each rod having a substantially v-shaped retractor blade retainer to retain each retractor blade in operative position during a surgical procedure once each retractor blade is adjusted relative to said retractor support frame; and a retractor coupling assembly including a retractor connector adjustably coupled to said retractor support frame by a support frame mount to operatively position and maintain said radially adjustable retractor blades in place during the surgical procedure.

10. The surgical tissue retractor of claim wherein said retractor connector comprises an elongated arm coupled at opposite end portions to said support frame mount and a sternal retractor mount, said support frame mount comprises a housing affixed to said retractor support frame including a concave recess that receives and seats at least a portion of a convex member therein and an internally threaded hole extending from a surface of said convex member to said concave recess to receive an externally threaded fastener to engage said convex member when positioned in said concave recess to selectively position and retain said retractor support frame in position relative to said elongated arm and said sternal retractor mount comprises a bracket including a slot to mount said surgical tissue retractor to a sternal retractor and a concave recess that receives and seats at least a portion of a convex member therein affixed to an interconnecting member and an internally threaded hole to receive an externally threaded fastener to secure at least a portion of said convex member in said concave recess.

11. The surgical tissue retractor of claim 10 wherein each said interconnecting member includes a hole formed therethrough to receive a portion of said elongated arm such that said elongated arm is adjusted relative thereto and an internally threaded hole to receive an externally threaded fastener to secure said interconnecting member in place on said elongated arm.

12. The surgical tissue retractor of claim 9 wherein each said radially adjustable retractor blade comprises a valve engaging blade element including a pendant member affixed to the corresponding elongated rod by an upper mounting member and a lower valve retainer to engage and retain the heart valve open during a surgical procedure.

13. The surgical tissue retractor of claim 12 wherein each said lower valve retainer comprises an upwardly flared skirt including an arcuate valve engaging surface disposed outwardly in spaced relationship relative to said pendant member and beneath said upper mounting member.

14. A surgical tissue retractor for use in aortic or pulmonary valve surgery comprising a retractor assembly including a retractor support frame having an outer periphery, a plurality of radially adjustable retractor blades configured to engage and retain a heart valve open during a surgical procedure mounted on said retractor support frame, each retractor blade including a corresponding elongated rod positioned in a corresponding hole or channel formed in the retractor support frame and each rod having a substantially v-shaped retractor blade retainer to retain each retractor blade in operative position during a surgical procedure once each retractor blade is adjusted relative to said retractor support frame; and a retractor coupling assembly including a retractor connecting member pivotally mounted on the retractor support frame by a support frame mount, and a sternal retractor mount capable of being coupled to a sternal retractor.

15. The surgical tissue retractor of claim 14 wherein each radially adjustable retractor blade comprises a valve engaging blade element coupled to said retractor support frame by the corresponding elongated rod extending through the corresponding hole or channel formed through said retractor support frame.

16. The surgical tissue retractor of claim 14 wherein said retractor connecting member comprises an elongated arm or member coupled at opposite end portions to said support frame mount and said sternal retractor mount.

17. The surgical tissue retractor of claim 16 wherein said support frame mount comprises a housing affixed to said retractor support frame including a concave recess or seat that receives and seats at least a portion of a convex member therein and an internally threaded hole or channel extending from a surface of said convex member to said concave recess or seat to receive an externally threaded fastener to engage said convex member when positioned in said concave recess or seat to selectively position and retain said retractor support frame in position relative to said elongated arm or member.

18. The surgical tissue retractor of claim 17 wherein said sternal retractor mount comprises a bracket including a slot or channel to mount said surgical tissue retractor to a sternal retractor and a concave recess or seat that receives and seats at least a portion of a convex member therein affixed to an interconnecting member and an internally threaded hole or channel to receive an externally threaded fastener to secure at least a portion of said convex member in said concave recess or seat and said interconnecting member includes a channel or hole formed therethrough to receive a portion of said elongated arm or member such that said elongated arm or member is adjusted relative thereto and an internally threaded channel or hole to receive an externally threaded fastener to secure said interconnecting member in place on said elongated arm or member.

* * * * *